United States Patent [19]

Berg

[11] Patent Number: 5,453,166
[45] Date of Patent: Sep. 26, 1995

[54] SEPARATION OF ETHANOL FROM 2-BUTANONE BY EXTRACTIVE DISTILLATION

[75] Inventor: Lloyd Berg, 1314 S. Third Ave., Bozeman, Mont. 59715

[73] Assignee: Berg; Lloyd, Bozeman, Mont.

[21] Appl. No.: 335,176

[22] Filed: Nov. 7, 1994

[51] Int. Cl.⁶ .................................................. B01D 3/40
[52] U.S. Cl. .............................. 203/57; 203/58; 203/59; 203/60; 203/62; 203/63; 203/64; 203/65; 203/67; 203/69; 203/70; 568/410; 568/913
[58] Field of Search ...................... 203/69, 70, 65, 203/64, 63, 60, 62, 58, 67, 59, 57, 78, 84; 568/410, 913, 918

[56] References Cited

U.S. PATENT DOCUMENTS

| | | | |
|---|---|---|---|
| 2,528,761 | 11/1950 | Lake et al. | 203/69 |
| 2,570,205 | 10/1951 | Carlson et al. | 203/58 |
| 2,583,412 | 1/1952 | Carlson et al. | 203/84 |
| 2,591,712 | 4/1952 | Morrell et al. | 203/84 |
| 2,591,714 | 4/1952 | Morrell | 203/84 |
| 2,617,757 | 11/1952 | Michael | 568/913 |

*Primary Examiner*—Wilbur Bascomb, Jr.

[57] ABSTRACT

Ethanol is impossible to separate from 2-butanone by conventional distillation or rectification because of the minimum boiling azeotrope between these two. Ethanol can be readily separated from 2-butanone by extractive distillation. Effective agents are dipromyl amine, phenol and dimethylsulfoxide.

2 Claims, No Drawings

5,453,166

SEPARATION OF ETHANOL FROM 2-BUTANONE BY EXTRACTIVE DISTILLATION

FIELD OF THE INVENTION

This invention relates to a method for separating ethanol from 2-butanone using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility an Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of oxygenated organic compounds, e.g. the Fischer-Tropsch process. Two of the commonest compounds in this mixture are ethanol and 2-butanone. Ethanol boils at 78.4° C. and 2-butanone at 79.6° C. The relative volatility between these two is 1.00 because they form an azeotrope which makes it impossible to separate them by conventional rectification. Extractive distillation would be an attractive method of effecting the separation of ethanol from 2-butanone if agents can be found that (1) will create a large apparent relative volatility between ethanol and 2-butanone and (2) are easy to recover from ethanol or 2-butanol. Table 2 shows the relative volatility required to obtain 99% purity. With an agent giving a relative volatility of 2.1, only 18 plates are required.

TABLE 2

Theoretical and Actual Plates Required vs. Relative Volatility for Ethanol-2-Butanone Separation

| Relative Volatility | Theoretical Plates Required At Total Reflux, 99% Purity | Actual Plates Rquired 75% Efficiency |
|---|---|---|
| 1.25 | 42 | 56 |
| 1.5 | 23 | 31 |
| 2.0 | 14 | 19 |
| 2.1 | 13 | 18 |

OBJECTIVE OF THE INVENTION

The object of this invention is to provide a process or method of extractive distillation that will enhance the relative volatility of ethanol from 2-butanone in their separation in a rectification column.

It is a further object of this-invention to identify organic compounds which in addition to the above contraints are stable, can be separated from ethanol and recycled to the extractive column with little decomposition.

SUMMARY OF THE INVENTION

The objects of this invention are to provide a process for separating ethanol from 2-butanone which entails the use of certain organic compounds as the agent in extractive distillation.

DETAILED DESCRIPTION OF THE INVENTION

I have discovered that certain organic compounds will greatly improve the relative volatility of ethanol to 2-butanone and permit the separation of ethanol from isopropanol by rectification when employed as the agent in extractive distillation. Table 3 lists the compounds that I have found to be effective. They are toluene, ethyl benzene, p-xylene, m-xylene, o-xylene, cumene, p-cymene, 1-pentene, phenol, tetrahydronaphthalene, p-cresol, o-cresol, m-cresol, 4-ethyl phenol, 3-ethyl phenol, 2-isopropyl phenol, 3-isopropyl phenol, o-sec. butyl phenol, 2-tert. butyl phenol, 2,4-dimethyl phenol, 4-tert-butyl phenol,

TABLE 3

Effective Extractive Distillation Agents For Separating Ethanol From 2-Butanone

| Compounds | Relative Volatility |
|---|---|
| None | 1.00 |
| Toluene | 1.35 |
| Ethyl benzene | 1.4 |
| p-Xylene | 1.45 |
| m-Xylene | 1.55 |
| o-Xylene | 1.55 |

TABLE 3-continued

Effective Extractive Distillation Agents For
Separating Ethanol From 2-Butanone

| Compounds | Relative Volatility |
| --- | --- |
| Cumene | 1.45 |
| p-Cymene | 1.5 |
| 1-Pentene | 2.0 |
| Tetrahydro naphthalene | 1.35 |
| Phenol | 2.0 |
| p-Cresol | 1.55 |
| o-Cresol | 1.7 |
| m-Cresol | 1.55 |
| 4-Ethyl phenol | 1.5 |
| 3-Ethyl phenol | 1.35 |
| 2-Isopropyl phenol | 1.35 |
| 3-Isopropyl phenol | 1.5 |
| o-sec. Butyl phenol | 1.45 |
| 2-tert-Butyl phenol | 1.7 |
| 2,4-Dimethyl phenol | 1.45 |
| 4-tert-Butyl phenol | 1.35 |
| Diethylene glycol methyl ether | 1.4* |
| Diethylene glycol ethyl ether | 1.25* |
| Dipropylene glycol methyl ether | 1.45* |
| Anisole | 1.7 |
| Phenetole | 1.6 |
| Ethylene glycol dimethyl ether | 1.35 |
| Phenyl ether | 1.25 |
| 1,2-Methylene dioxybenzene | 1.7 |
| Ethyl-3-ethoxy propionate | 1.3 |
| 2-Hydroxyacetophanone | 1.5 |
| Ethylene carbonate | 1.25 |
| Pronylene carbonate | 1.35 |
| 1,1,2-Trichloroethane | 1.8 |
| 2,2,2-Trichloroethanol | 1.4 |
| Chlorobenzene | 1.65 |
| m-Dichlorobenzene | 1.45 |
| Dimethylacetamide | 1.45 |
| n-Butyl amine | 1.8 |
| N-(2-Hydroxyethyl)-2-pyrrolidinone | 1.7 |
| 1-Methyl piperazine | 1.8* |
| Benzonitrile | 1.55 |
| N-Cyclo hexyl-2-pyrrolidinone | 1.45 |
| 1,1,3,3-Tetramethyl urea | 1.5 |
| N,N-Dimethyl ethanol amine | 1.65 |
| 1-Formyl piperidine | 1.25 |
| N,N-Dimethyl aniline | 1.5 |
| N(N,N-Dimethylamino)-propyl-2-pyrrolidinone | 1.6 |
| Cyclohexyl amine | 1.5* |
| Dipropyl amine | 2.0 |
| N-Ethyl aniline | 1.6 |
| Triethyl amine | 1.55 |
| N-Ethyl morpholine | 1.25 |
| 3-Dimethylamine propyl amine | 1.45 |
| 3-Methyl pentamethylene diamine | 1.6 |
| Formamide | 1.5 |
| Benzyl cyanide | 1.5 |
| n-Butyronitrile | 1.55 |
| Adiponitrile | 1.6 |
| Nitroethane | 1.9 |
| 1-Nitropropane | 2.0 |
| 2-Nitropropane | 1.75 |
| 2-Nitrotoluene | 1.45 |
| 3-Nitrotoluene | 1.55 |
| Nitrobenzene | 1.75 |
| 1-Methyl-2-pyrrolidinone | 1.4* |
| 2-Pyrrolidinone | 1.6* |
| Methyl benzoate | 1.3 |
| Ethyl benzoate | 1.5 |
| Dimethylsulfoxide | 2.1*# |

*Brings 2-butanone out as overhead product
Data from multiplate rectification column diethylene gylcol methyl ether, diethylene glycol ethyl ether, dipropylene glycol methyl ether, anisole, phenetole, ethylene glycol dimethyl ether, phenyl ether, 1,2-methylene dioxybenzene, ethyl-3-ethoxy propionate, 2-hydroxyacetophenone, ethylene carbonate, propylene carbonate, 1,1, 2-trichloroethane, 2,2,2-trichloroethanol, chlorobenzene, m-dichlorobenzene, dimethylacetamide, n-butyl amine, N-(2-hydroxyethyl)-2-pyrrolidinone, 1-methyl piperazine, benzonitrile, N-cyclohexyl-2-pyrrolidinone, ]1,3,3-tetramethylurea, N,N-dimethyl ethanol amine, 1-formyl piperidine, N-(N,N-dimethylamino)-propyl-2-pyrrolidinone, cyclohexyl amine, dipropyl amine, n-ethyl aniline, triethyl amine, N-ethyl morpholine, 3-dimethylamine propyl 3-methyl pentamethylene aiamine, formamide, benzyl cyanide, n-butyronitrile, adiponitrile, nitroethane, 1-nitropropane, 2-nitropropane, 2-nitrotoluene, 3-nitrotoluene, nitrobenzene, 1-methyl-2-pyrrolidinone, 2-pyrrolidinone, methyl benzoate, ethyl benzoate, dimethylsulfoxide and N,N-dimethylaniline.

THE USEFULNESS OF THE INVENTION

The usefulness or utility of this invention can be demonstrated by referring to the data presented in Tables 1–3. All of the successful agents show that ethanol can be separated from 2-butanone by means of extractive distillation in a rectification column and that the ease of separation as measured by relative volatility is considerable.

WORKING EXAMPLES

Example 1

Sixteen grams of ethanol, 24 grams of 2-butanone and 40 grams of dipropyl amine were charged to a vapor-liquid equilibrium still and refluxed for five hours. Analysis indicated a vapor composition of 76.4% ethanol, 23.6% 2-butanone; a liquid composition of 61.3% ethanol, 38.7% 2-butanone. This is a relative volatility of ethanol to 2-butanone of 2.0.

Example 2

A solution comprising 50 grams of ethanol and 100 grams of 2-butanone was placed in the stillpot of a 5.6 theoretical plate glass perforated plate rectification column. When refluxing began, an extractive agent comprising dimethylsulfoxide was pumped into the top of the column at a rate of 15 ml/min. The temperature of the extractive agent as it entered the column was 74° C. After establishing the feed rate of the extractive agent, the heat input to the ethanol-2-butanone in the stillpot was adjusted to give a total reflux rate of 40 ml/min. After 1.5 hours of operation overhead and bottoms samples were collected and analysed. The overhead composition was 6.2% ethanol, 93.8% 2-butanone and the bottoms composition was 79.9% ethanol, 20.1% 2-butanone. This gives a relative volatility of 2-butanone to ethanol of 2.1 for each theoretical plate.

I claim:

1. A method for recovering ethanol from a mixture of ethanol and 2-butanone which comprises distilling a mixture of ethanol and 2-butanone in the presence of about one part by weight of an extractive agent per part of ethanol-2-butanone mixture, recovering the ethanol as overhead product and obtaining the 2-butanone and the extractive agent as bottoms product, wherein said extractive agent consists of one material selected from the group consisting of anisole, phenetole, ethylene glycol dimethyl ether, phenyl ether, 1,2-methylene dioxybenzene, ethyl-3-ethoxy propionate, 2-hydroxyacetophenone, ethylene carbonate, propylene carbonate, 1,1,2-trichloroethane, 2,2,2-trichloroethanol, chlorobenzene, m-dichlorobenzene, dimethylacetamide, n-butyl amine, N-(2-hydroxyethyl)-2-pyrrolidinone, 1-methyl piperazine, benzonitrile, N-cyclohexyl-2-pyrrolidinone, 1,1,3,3-tetramethyl urea, N,N-dimethyl ethanol amine, 1-formyl piperidine, N,N-dimethyl aniline, dipropyl amine, N(N,N-dimethylamino)-propyl-2-pyrrolidinone, n-ethyl aniline, triethyl amine, N-ethyl morpholine, 3-dimethylamine propyl amine, formamide, 3-methyl pentamethylene diamine, benzyl cyanide, n-butyronitrile, adiponitrile, nitroethane, 1-nitropropane, 2-nitropropane, 2-nitrotoluene, 3-nitrotoluene, nitrobenzene, methyl benzoate and ethyl benzoate.

2. A method for recovering 2-butanone from a mixture of 2-butanone and ethanol which comprises distilling a mixture of 2-butanone and ethanol in the presence of about one part of an extractive agent per part of 2-butanone-ethanol mixture, recovering the 2-butanone as overhead product and obtaining the ethanol and the extractive agent as bottoms product, wherein said extractive agent consists of one material selected from the group consisting of diethylene glycol methyl ether, diethylene glycol ethyl ether, dipropylene glycol methyl ether, 1-methyl piperazine, cyclohexyl amine, 1-methyl-2-pyrrolidinone, 2-pyrrolidinone and dimethylsulfoxide.

* * * * *